US006984809B2

(12) United States Patent
Lin et al.

(10) Patent No.: US 6,984,809 B2
(45) Date of Patent: Jan. 10, 2006

(54) HEAT GENERATOR

(75) Inventors: Jhy-Chain Lin, Tu-Cheng (TW); Charles Leu, Fremont, CA (US)

(73) Assignee: Hon Hai Precision Industry Co., Ltd., (TW)

( * ) Notice: Subject to any disclaimer, the term of this patent is extended or adjusted under 35 U.S.C. 154(b) by 0 days.

(21) Appl. No.: 10/977,723

(22) Filed: Oct. 29, 2004

(65) Prior Publication Data
US 2005/0139687 A1 Jun. 30, 2005

(30) Foreign Application Priority Data
Dec. 26, 2003 (TW) ............... 92222756 U

(51) Int. Cl.
*H05B 3/28* (2006.01)
*H05B 1/02* (2006.01)
*G01N 25/18* (2006.01)

(52) U.S. Cl. ............... 219/385; 219/201; 219/494; 219/497; 374/44

(58) Field of Classification Search ............... 219/385, 219/386, 200, 201, 228, 494, 497; 62/3.2, 62/3.3, 3.7; 374/44
See application file for complete search history.

(56) References Cited

U.S. PATENT DOCUMENTS

| | | | | |
|---|---|---|---|---|
| 3,114,255 A | * | 12/1963 | Niven | ............... 374/44 |
| 3,662,587 A | * | 5/1972 | Allen et al. | ............... 374/44 |
| 3,733,887 A | * | 5/1973 | Stanley | ............... 374/44 |
| 4,929,089 A | | 5/1990 | Tsuchida | |
| 5,258,929 A | * | 11/1993 | Tsuchida | ............... 702/136 |
| 6,550,961 B1 | | 4/2003 | Ueda | |
| 2003/0072349 A1 | | 4/2003 | Osone et al. | |

FOREIGN PATENT DOCUMENTS

DE 2724846 A * 12/1978

* cited by examiner

*Primary Examiner*—Joseph Pelham
(74) *Attorney, Agent, or Firm*—Morris Manning & Martin; Tim Tingkang Xia, Esq.

(57) ABSTRACT

A heat generator includes a heat generating member and a temperature compensating member made from different material. The heat generating member includes a heat flow output face for outputing heat flow and five heat flow insulation faces. The temperature compensating member encloses and contacts the heat generating member except the heat flow output face. A heat flow compensating circuit is electrically connected between the temperature compensating member and the heat generating member for maintaining a state of no heat flow flowing between the heat generating member and the temperature compensating member, whereby the heat energy of the heat flow outputing from the heat flow output face is equal to the heat energy of heat generated by the heat generating member.

14 Claims, 1 Drawing Sheet

HEAT GENERATOR

CROSS-REFERENCE TO RELATED APPLICATIONS

This application is related to three copending U.S. patent applications entitled "HEAT GENERATOR", filed with the same assignee as the instant application and with application Ser. Nos. 10/930,551 filed on Aug. 31, 2004, 10/951,422 filed on Sep. 28, 2004, and 10/951,360 filed on Sep. 28, 2004, respectively. The disclosures of the above identified applications are incorporated herein by reference.

TECHNICAL FIELD

The present invention relates to a heat generator, and particularly to a heat generator having heat flow compensation capability.

BACKGROUND

When developing new material, especially heat conduct material, it need to measure the heat conductivity of the material. When designing a heat dissipation device for electronic devices, the designer need to know the heat conduct capability of the material of the heat dissipation device. Precisely measuring heat conductivity of the material is the key of the design.

In early times, the heat conductivity of a material is measured via sandwiching a specimen made from the material between a heat source and an object with a lower temperature. The heat generated by the heat source flows through the specimen to the object with lower temperature. A temperature gradient $\Delta T$ exists between two opposite ends of the specimen. The distance between the two opposite ends of the specimen $\Delta X$ can be measured. Assuming that all of the heat generated by the heat source flow through the specimen, the heat energy Q of the heat flow flowing through the specimen is equal to the heat energy Q' generated by the heat source. The heat energy Q' generated by the heat source is calculated according to the equation as follows:

$$Q' = \alpha I^2 R$$

wherein R is the resistance value of a thermal resistor embedded in the heat source, I represents the electric current flowing through the thermal resistor, and $\alpha$ is a ratio of electrical power converted to heat energy of the thermal resistor. The heat conductivity K of the material of the specimen can be calculated according to the equation as follows:

$$K = q \ast \Delta X / \Delta T$$

q represents heat flow which is the rate at which heat energy Q flows through the specimen per square meter, in $W/m^2$.

In the above method, the specimen firmly contact with one face of the heat source. The other faces of the heat source are heat insulated by a layer of insulation material covered thereon in order to ensure all of the heat generated by the heat source flow through the specimen. However, the insulation capability of the insulation material, such as alumina, is limited. Some of the heat generated by the heat source is inevitably dissipated through the other faces which do not contact the specimen. That means, the heat energy Q flowing through the specimen is not equal to the heat energy Q' generated by the heat source. Thus, the value of the heat flow q flowing through the specimen exists an inaccuracy which results in the calculated value of the heat conductivity K of the material of the specimen existing an inaccuracy.

SUMMARY OF THE INVENTION

Accordingly, an object of the present invention is to provide a heat generator which can output a predetermined heat flow precisely.

To achieve the above-mentioned object, a heat generator in accordance with the present invention comprises a heat generating member and a temperature compensating member made from different material. The heat generating member comprises a heat flow output face for outputting heat flow and a plurality of heat flow insulation faces. The temperature compensating member encloses and contacts the heat generating member except the heat flow output face thereof. A heat flow compensating circuit is electrically connected between the temperature compensating member and the heat generating member for maintaining a state of no heat flow flowing between the heat generating member and the temperature compensating member, whereby the heat energy of the heat flow outputting from the heat flow output face is equal to the heat energy of heat generated by the heat generating member.

Other objects, advantages and novel features of the present invention will be drawn from the following detailed description of a preferred embodiment of the present invention with attached drawings, in which:

DESCRIPTION OF A PREFERRED EMBODIMENT

Figure 1:
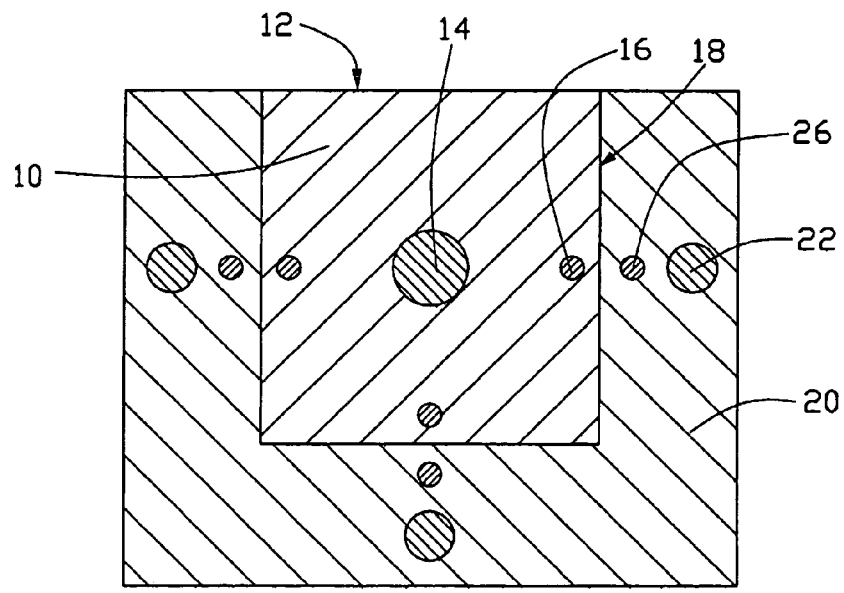
FIG. 1 is an exploded view of a heat generator in accordance with an embodiment of the present invention.

Referring to FIG. 1, a heat generator in accordance with the preferred embodiment of the present invention comprises a beat generating member 10 and a temperature compensating member 20.

The heat generating member 10 is a polyhedron and made from material with a higher heat conductivity. In the preferred embodiment, we take a cube shape employed as an example of the heat generating member 10. The heat generating member 10 comprises six faces. One face 12 is used as a heat flow output face and the other five faces are used as heat flow insulation faces that no heat flow flows therethrough. A thermal resistor 14 is embedded in the heat generating member 10 for generating a predetermined heat energy. The quantity Q' of the heat energy generated by the thermal resistor is calculated according to the following equation $$Q' = \alpha I^2 R.$$

wherein R is the resistance value of the thermal resistor 14, I represents the electric current flowing through the thermal resistor 14, and $\alpha$ is a ratio of electrical power converted to heat energy. A first thermistor 16 is installed in the heat generating member 10 adjacent each heat flow insulation face of the heat generating member 10 for sensing the temperature of the heat flow insulation face.

The temperature compensating member 20 is made from material with a lower heat conductivity in comparison with the higher heat conductivity of the heat generating member 10. The temperature compensating member 20 is cube shape and comprises four side walls and a bottom wall cooperatively forming a cavity therebetween. The heat generating member 10 is accommodated within the cavity with each of the walls of the temperature compensating member 20 intimately contacting with a corresponding heat flow insulation face of the heat generating member 10. An interface 18 is therefore formed between each heat flow insulation face of the heat generating member 10 and the corresponding wall of the temperature compensating member 20. A thermal resistor 22 is embedded in each of the walls of the temperature compensating member 20. When electrified the thermal resistor 22 generates heat. A second thermistor 26 is installed in each of the walls of the temperature compensating member 20 adjacent the interface 18, for sensing the temperature thereof.

Figure 2:
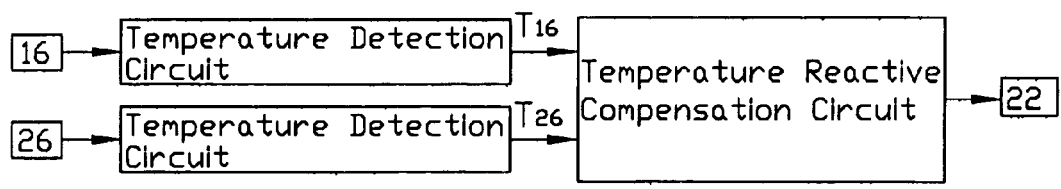
FIG. 2 is a diagram showing the heat flow compensating circuit of the heat generator.

FIG. 2 shows a heat flow compensating circuit electrically connected between the thermistors 16, 26 and the thermal resistor 22. The heat flow compensating circuit comprises two temperature detection circuits electrically connected to the thermistors 16, 26 respectively, and a temperature reactive compensating circuit electrically connected to the thermal resistor 22. The two temperature detection circuits are used to sense the temperature of the heat flow insulation face of the heat generating member 10 and the temperature compensating member 20 adjacent the interface 18 and output a pair of corresponding temperature signals T16, T26 to the temperature reactive compensating circuit. When the temperature of the temperature compensating member 20 adjacent the interface 18 is not equal to that of the heat flow insulation face of the heat generating member 10, the temperature reactive compensating circuit outputs an adjusted current to the thermal resistor 22 of the temperature compensating member 20 to adjust the temperature of the temperature compensating member 20 adjacent the interface 18 to thereby cause it to be equal to the temperature of the heat flow insulation face of the heat generating member 10. Thus, no heat flow flows between the heat flow insulation face of the heat generating member 10 and the temperature compensating member 20 and all of the heat generated by the heat generating member 10 is transferred from the heat flow output face 12 of the heat generating member 10 to a specimen (not shown). Therefore, the heat energy Q flowing through the specimen is equal to the heat energy Q' generated by the heat generating member 10, and a predetermined heat flow is able to be precisely transferred from the heat generator.

In the present invention, the heat generating member 10 is accommodated in the cavity of the temperature compensating member 20 and the walls of the temperature compensating member 20 surround and contact the heat flow insulation faces of the heat generating member 10. Since the heat generating member 10 and the temperature compensating member 20 are made from different material, great heat resistance is therefore formed at the interfaces 16 between the heat flow insulation faces of the heat generating member 10 and the walls of the temperature compensating member 20. Thus, no additional heat insulation member is required to be installed between the heat generating member 10 and the temperature compensating member 20.

It is understood that the invention may be embodied in other forms without departing from the spirit thereof. Thus, the present example and embodiment is to be considered in all respects as illustrative and not restrictive, and the invention is not to be limited to the details given herein.

What is claimed is:
1. A heat generator comprising:
a heat generating member for generating heat, comprising a heat flow output face and a plurality of heat flow insulation faces;
a temperature compensating member enclosing and contacting the heat generating member except the heat flow output face thereof, the temperature compensating member and the heat generating member being made from different material; and
a heat flow compensating circuit electrically connected between the temperature compensating member and the heat generating member for maintaining a state of no heat flow flowing between the heat generating member and the temperature compensating member, whereby the heat energy of the heat flow outputting from the heat flow output face is equal to the heat energy of the heat generated by the heat generating member.

2. The heat generator as claimed in claim 1, wherein an interface is formed between the heat generating member and the temperature compensating member, and two thermistors are respectively provided in the heat generating member and the temperature compensating member adjacent the interface.

3. The heat generator as claimed in claim 2, wherein a thermal resistor is installed in the temperature compensating member.

4. The heat generator as claimed in claim 3, wherein the heat flow compensating circuit comprises two temperature detection circuits connected to the two thermistors respectively for sensing the temperature of the heat generating member and the temperature compensating member adjacent the interface, and a temperature reactive compensating circuit connected to the temperature compensating member for outputting an adjusted current to the thermal resistor thereof when the temperature of the heat generating member and the temperature compensating member adjacent the interface are not equal to each other, to adjust the temperature of the temperature compensating member adjacent the interface to cause it to be equal to the temperature of the heat generating member adjacent the interface.

5. The heat generator as claimed in claim 4, wherein the heat generating member is a polyhedron.

6. The heat generator as claimed in claim 5, wherein the heat generating member is a cube with five heat flow insulation faces.

7. The heat generator as claimed in claim 6, wherein the temperature compensating member comprises five walls with a cavity formed therebetween, the heat generating member being received in the cavity with each of the walls contacting a corresponding one of the heat flow insulation faces.

8. A heat generator comprising:
a heat generating member with a higher heat conductivity for generating heat, comprising a heat flow output face;
a single integrally formed temperature compensating member with a lower heat conductivity, enclosing the heat generating member except the heat flow output face thereof; and
a heat flow compensating circuit electrically connected between the temperature compensating member and the heat generating member for maintaining a state of no heat flow flowing between the heat generating member and the temperature compensating member, whereby the heat energy of the heat flow outputting from the heat flow output face is equal to the heat energy of the heat generated by the heat generating member.

9. The heat generator as claimed in claim 8, wherein the temperature compensating member contacts the heat generating member.

10. The heat generator as claimed in claim 9, wherein two thermistors are respectively provided in the heat generating member and the temperature compensating member adjacent an interface formed therebetween.

11. The heat generator as claimed in claim 10, wherein a thermal resistor is installed in the temperature compensating member.

12. The heat generator as claimed in claim 11, wherein the heat flow compensating circuit comprises two temperature detection circuits connected to the two thermistors respectively for sensing the temperature of the heat generating member and the temperature compensating member adjacent the interface, and a temperature reactive compensating circuit connected to the thermal resistor of the temperature compensating member for outputting an adjusted current to the thermal resistor, when the temperature of the heat generating member and the temperature compensating member adjacent the interface are not equal to each other, to adjust the temperature of the temperature compensating member adjacent the interface to cause it to be equal to the temperature of the heat generating member adjacent the interface.

13. A method to provide heat to an object, comprising:
providing a heat generating member with a higher heat conductivity for generating heat provided to an object;
providing a temperature compensating member with a lower heat conductivity to surround said heat generating member except a face of said heat generating member confronting with said object so as to form a heat-transmitting difference interface between said heat generating member and said temperature compensating member;
sensing temperature of said temperature compensating member and temperature of surfaces of said heat generating member surrounded by said temperature compensating member; and
adjusting said temperature of said temperature compensating member so as to provide a heat transmission balance across said interface.

14. The method as claimed in claim 13, wherein a thermal resistor is installed respectively in said heat generating member and said temperature compensating member to adjust temperatures thereof.

* * * * *